United States Patent [19]

Thomson

[11] Patent Number: 5,498,712
[45] Date of Patent: Mar. 12, 1996

[54] TRIPHENODIOXAZINE DYES

[75] Inventor: Gordon A. Thomson, Bolton, England

[73] Assignee: Zeneca Limited, London, England

[21] Appl. No.: 60,049

[22] Filed: May 13, 1993

[30] Foreign Application Priority Data

May 26, 1992 [GB] United Kingdom .................. 9211110

[51] Int. Cl.⁶ .................. C07D 498/04; C09B 19/00; C09B 62/04; C09B 62/503

[52] U.S. Cl. .................. 544/76; 544/75; 544/77; 8/436; 8/543; 8/549

[58] Field of Search .................. 544/75, 76, 77; 8/436, 543, 544

[56] References Cited

U.S. PATENT DOCUMENTS

| | | | |
|---|---|---|---|
| 2,092,399 | 9/1937 | Kranzlein et al. | 544/74 |
| 4,588,810 | 5/1986 | Harms et al. | 544/76 |
| 4,665,179 | 5/1987 | Wunderlich et al. | 544/75 |
| 4,785,098 | 11/1988 | Fuchs et al. | 544/76 |
| 4,786,728 | 11/1988 | Schwaiger et al. | 544/76 |
| 4,874,857 | 10/1989 | Harms | 544/75 |
| 5,126,450 | 6/1992 | Smith | 544/76 |

FOREIGN PATENT DOCUMENTS

| | | |
|---|---|---|
| 158882 | 3/1985 | European Pat. Off. . |
| 133270 | 8/1985 | European Pat. Off. . |
| 204245 | 5/1986 | European Pat. Off. . |
| 205080 | 6/1986 | European Pat. Off. . |
| 205079 | 6/1986 | European Pat. Off. . |
| 299328 | 1/1989 | European Pat. Off. . |
| 349848 | 1/1990 | European Pat. Off. . |
| 356014 | 2/1990 | European Pat. Off. . |
| 482789 | 4/1992 | European Pat. Off. . |
| 2503611 | 8/1975 | Germany . |
| 3148889 | 6/1983 | Germany . |
| 3503564 | 8/1986 | Germany . |
| 3625346 | 1/1988 | Germany . |
| 1559752 | 1/1980 | United Kingdom . |

*Primary Examiner*—Philip I. Datlow
*Attorney, Agent, or Firm*—Cushman Darby & Cushman

[57] ABSTRACT

A water-soluble triphenodioxazine dye having a chloro or bromo atom at one of the 6- and 13-positions and a group of Formula (1) at the remaining 6- or 13-position:

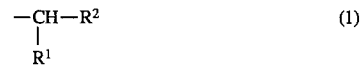

wherein:

$R^1$ is H, OH or $CH_3$; and $R^2$ is $C_{1-3}$-alkyl, hydroxy-$C_{1-3}$-alkyl or $-CH_2-(C_{1-4}$-alkyl).

The dyes are useful for the coloration of textile materials.

11 Claims, No Drawings

TRIPHENODIOXAZINE DYES

This invention relates to triphenodioxazine (TPD) dyes, especially TPD reactive dyes, their preparation and use.

TPD reactive dyes having chloro atoms at the 6- and 13-positions are known from GB patent 1,450,746 and are useful for colouring a wide range of textile materials, particularly cellulosic materials, by forming a covalent bond thereto. There is a strong demand for TPD dyes having good dyeing properties, particularly those having good water-solubility which can be used to prepare high-strength liquid dye formulations.

According to the present invention there is provided a water-soluble triphenodioxazine dye having a chloro or bromo atom at one of the 6- and 13-positions and a group of Formula (1) at the remaining 6- or 13-position:

wherein:

$R^1$ is H, OH or $CH_3$; and $R^2$ is $C_{1-3}$-alkyl, hydroxy-$C_{1-3}$-alkyl or —$CH_2O$—($C_{1-4}$-alkyl).

Preferably $R^1$ is H or methyl, especially H. $R^2$ is preferably $C_{1-3}$-alkyl, especially methyl. In a preferred embodiment $R^1$ is H and $R^2$ is methyl.

As Examples of groups of Formula (1) there may be mentioned —$CH_2CH_3$, —$CH_2CH_2CH_3$, —$(CH_2)_3$—$CH_3$, —$CH_2CH(CH_3)_2$, —$CH(CH_3)_2$, —$CH_2CH_2$—O—$CH_3$, —$CH_2CH_2$—$OCH_2CH_3$, —$CH(OH)CH_3$ and —$CH_2CH_2OH$, the latter two exemplifying hydroxy-$C_{1-3}$-alkyl groups.

The TPD dye according to the invention preferably has a sulpho substituent at one or two of the 1-, 2-, 4-, 8-, 9- and 11-positions.

It is preferred that the TPD dye according to the invention is a reactive dye, this may be achieved by the presence of a fibre-reactive group attached to one or more of the 1-, 2-, 3-, 4-, 8-, 9-, 10- and 11-positions, more preferably at one or both of the 3- and 10-positions.

A preferred water-soluble dye according to the invention is of the Formula (2) or salt thereof:

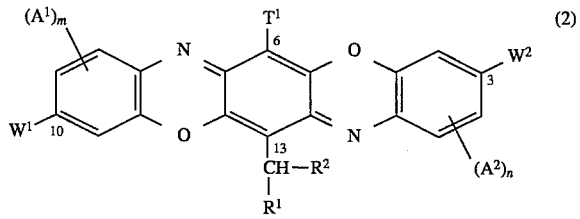

wherein:

$T^1$ is Cl or Br;

each $A^1$ and $A^2$ independently is alkyl, alkoxy, Cl, Br, carboxy, or —$SO_2$—Y;

each Y independently is —$OR^3$, —$NR^3R^4$, vinyl, a group convertible to vinyl on treatment with aqueous alkali, or optionally substituted alkyl;

each $R^3$ and $R^4$ independently is hydrogen, optionally substituted alkyl or aryl;

m and n are each independently 0, 1, 2 or 3;

$W^1$ and $W^2$ are each independently a fibre-reactive group or a group which is not fibre-reactive; and $R^1$ and $R^2$ are as hereinbefore defined.

The numbers indicated around the TPD ring system in Formula (2) serve to illustrate conventional ring numbering of TPD dyes.

$T^1$ is preferably Cl.

It is preferred that each $A^1$ and $A^2$ independently is selected from $C_{1-4}$-alkyl, $C_{1-4}$-alkoxy, Cl, Br, carboxy and —$SO_2$—Y. Preferably at least one of the groups represented by $A^1$ and at least one of the groups represented by $A^2$ is sulpho.

When Y is optionally substituted alkyl it is preferably $C_{1-4}$-alkyl. It is, however, preferred that Y is —OH or —$CH=CH_2$ or a group convertible to vinyl on treatment with aqueous alkali.

It is preferred that each $R^3$ and $R^4$ independently is selected from hydrogen, $C_{1-4}$-alkyl, phenyl and sulphophenyl.

m and n preferably have a value of 1 or 2.

It is preferred that one or both of $W^1$ and $W^2$ is a fibre-reactive group.

When $W^1$ and $W^2$ are both groups which are not fibre-reactive m and/or n preferably have a value of 1, 2 or 3 and it is preferred that at least one group represented by $A^1$ or $A^2$ is of formula —$SO_2$—$Y^1$ wherein $Y^1$ is vinyl or a group convertible to vinyl in the presence of aqueous alkali.

When only one of $W^1$ and $W^2$ is a group which is not fibre-reactive it is preferably H, halo, carboxy, sulpho, $C_{1-4}$-alkyl, or an ether, thioether or amine group. Preferred ether, thioether and amine groups are of the formula —$X^1$—Q wherein $X^1$ is O, S or $NR^5$ in which $R^5$ is the residue of a 1,4-piperidinyl group or preferably H or $C_{1-4}$-alkyl; and Q is optionally substituted $C_{1-4}$-alkyl or optionally substituted phenyl. The optional substituent which may be present on Q is preferably selected from hydroxy, carboxy, sulpho, halo, nitro, $C_{1-4}$-alkyl, amino and $C_{1-4}$-alkoxy.

When $W^1$ and $W^2$ are both groups which are not fibre-reactive it is preferred that at least one of $W^1$ and $W^2$ is an ether, thioether or amine group as hereinbefore defined.

Compounds where $W^1$ and $W^2$ are both of formula —$X^1$—Q wherein $X^1$ is as hereinbefore defined and Q is $C_{1-4}$-alkyl or phenyl having an acylatable substituent (e.g. hydroxy or amino) are useful as dyes for paper or as intermediates which may be condensed with acylating agent in the presence of an acid binding agent to introduce a fibre-reactive group onto the hydroxy or amino group. For example, when —$X^1$—Q is 2-aminoethylamino condensation with 2',5'-disulphoanilinodichloro-1,3,5-triazine at pH 8–9 yields a reactive dye having a chlorotriazine group.

The fibre-reactive group may be any group which is capable under alkaline conditions of forming a covalent bond between cellulose and the TPD dye. A preferred fibre-reactive group is of the formula:

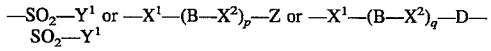

wherein:

$Y^1$ is vinyl or a group convertible to vinyl on treatment with aqueous alkali;

$X^1$ and $X^2$ are each independently O, S or $NR^5$;

B is a divalent organic linking group;

Z is a heterocyclic reactive group;

D is optionally substituted phenylene or naphthylene;

p and q are each independently 0 or 1; and each $R^5$ is as hereinbefore defined.

As examples of groups convertible to vinyl on treatment with aqueous alkali there may be mentioned —$CH_2CH_2$—$OSO_3H$, —$CH_2CH_2$—$SSO_3H$ and salts thereof.

$X^1$ is preferably —$NR^5$—, especially —NH—.

$X^2$ is preferably —$NR^5$—, especially —NH—.

p is preferably 1.

q is preferably 0.

The preferred heterocyclic reactive group represented by Z contains 1, 2 or 3 nitrogen atoms in the heterocyclic ring and at least one labile substituent on a carbon atom of the ring. A labile substituent is a substituent capable of being displaced by the hydroxy group of cellulose under alkaline conditions to form a covalent bond between said carbon atom and the cellulose.

As examples of heterocyclic reactive groups there may be mentioned:
2:3-dichloroquinoxaline-5- or -6-sulphonyl,
2:3-dichloroquinoxaline-5- or -6-carbonyl,
2:4-dichloroquinazolin-6- or -7-sulphonyl,
2:4:6-trichloroquinazolin-7- or -8-sulphonyl,
2:4:7- or 2:4:8-trichloroquinazolin-6-sulphonyl,
2:4-dichloroquinazolin-6-carbonyl,
1:4-dichlorophthalazine-6-carbonyl,
4:5-dichloropyridazon-1-yl-ethylcarbonyl,
2:4-dichloropyrimidine-5-carbonyl,
4-(4':5'-dichloropyridaz-6'-on-1'-yl)benzoyl,
2-chlorobenzthiazole-6-carbonyl,
3,6-dichloropyrazin-4-carbonyl,
4-(4':5'-dichloropyridaz-6'-on-1'-yl)phenylsulphonyl;
activated 4,6-dihalopyridin-2-yl and 2,6-dihalopyridin-4-yl groups such as:
3,4,5,6-tetrafluoropyridin-2-yl,
2,3,5,6-tetrafluoropyridin-4-yl,
2,4,6-trifluoro-3-cyanopyridin-4-yl,
2,5,6-trichloro-3-cyanopyridin-4-yl,
2,6-difluoro-3-cyano-5-chloropyridin-4-yl,
and especially pyrimidinyl and triazinyl groups having a labile substituent.

The preferred pyrimidinyl groups are pyrimidin-2-yl or -4-yl groups having a labile substituent, especially Cl, Br or F, in at least one of the remaining 2-, 4- and 6-positions. The 5-position may carry a substituent such as Cl or CN which is not normally labile but may enhance the reactivity of substituents in other positions of the pyrimidine ring. As specific examples of such pyrimidinyl groups there may be mentioned:
2,6-dichloropyrimidin-4-yl,
4,6-dichloropyrimidin-2-yl,
2,5,6-trichloropyrimidin-4-yl,
4,5,6-trichloropyrimidin-2-yl,
5-chloro-2-methylsulphonyl-6-methylpyrimidin-4-yl,
2,6-dichloro-5-cyanopyrimidin-4-yl,
4,6-dichloro-5-cyanopyrimidin-2-yl,
2,6-difluoro-5-chloropyrimidin-4-yl,
4,6-difluoro-5-chloropyrimidin-2-yl,
2,6-difluoro-5-cyanopyrimidin-4-yl,
4,6-difluoro-5-cyanopyrimidin-2-yl.

The preferred triazinyl group is a triazin-2-yl group having a labile substituent at one or both of the 4- and 6-positions. In this instance a wide range of labile substituents may be used such as activated aryloxy or various groups linked through a sulphur atom, e.g. $SO_3H$. However, preferred labile substituents are halogens, such as F, Br and especially Cl and quaternary ammonium groups such as tri-lower alkyl ammonium, e.g. $(CH_3)_3N^+$— and pyridinium groups, especially those derived from pyridine carboxylic acids, in particular 3-carboxypyridinium and 4-carboxypyridinium.

The triazinyl group having a labile substituent at only one of the 4- and 6-positions has a non-labile substituent in the remaining 4- or 6-position.

Examples of such non-labile substituents include alkylthio and arylthio groups, alkoxy and aryloxy groups and optionally substituted amino groups.

Examples of preferred non-labile substituents are $C_{1-4}$-alkoxy, e.g. methoxy, ethoxy, n-propoxy and iso-propoxy, butoxy; lower alkoxy lower alkoxy, e.g. beta-methoxyethoxy, beta-ethoxyethoxy, phenoxy; sulphophenoxy; amino; $C_{1-4}$-alkylamino, e.g. methylamino, ethylamino, butylamino, di($C_{1-4}$-alkyl)amino, e.g. dimethylamino, diethylamino, methylethylamino, dibutylamino and groups of the latter two types in which the alkyl groups are substituted, in particular by OH, CN or $SO_3H$, e.g. beta-hydroxyethylamino, di(beta-hydroxyethyl)amino, beta-cyanoethylamino, di(beta-cyanoethyl)amino, beta-sulphoethylamino, beta-hydroxypropylamino, (beta-hydroxybutyl)ethylamino and (beta-hydroxyethyl)methylamino; cycloalkylamino, e.g. cyclohexylamino; cyclic amino, e.g. morpholino or piperazino; naphthylamino substituted by 1,2 or 3 $SO_3H$ groups and optionally substituted phenyl amino groups.

Preferred optionally substituted phenylamino groups are of the formula:

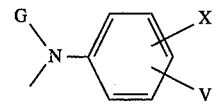

wherein G is H; $C_{1-4}$-alkyl, especially methyl or ethyl; substituted $C_{1-4}$-alkyl such as sulphomethyl and beta-carboxy-, beta-hydroxy- or beta-cyanoethyl; and V and X are each independently selected from H, COOH, $SO_3H$, $CH_3$, $C_2H_5$, $OCH_3$, $OC_2H_5$, Cl, Br, CN, $NO_2$ and $NHCOCH_3$.

The present invention also includes water-soluble dyes as hereinbefore described where the triazinyl group or groups represented by Z has or have non-labile substituents at both the 4- and 6- positions to give a reactive or non-reactive dye depending on the nature of the other substituents in the dye.

The divalent organic linking group represented by B is preferably alkylene, especially $C_{1-6}$-alkylene, more especially $C_{2-4}$-alkylene; aralkylene, preferably $C_{7-11}$-aralkylene, especially phenyl-$C_{1-4}$-alkylene; and arylene, preferably arylene having up to six carbon atoms, especially phenylene; which may be substituted or unsubstituted.

As examples of alkylene and aralkylene radicals represented by B, there may be mentioned:
ethylene
1,2- and 1,3-propylene
2-hydroxy-1,3-propylene
1- and 2-phenyl-1,3-propylene
2-(4'-sulphophenyl)-1,3-propylene
1,4-, 2,3- and 2,4-butylene
2-methyl-1,3-propylene
2-methyl-2,4-pentylene
2,2-dimethyl-1,3-propylene
1-phenylethylene
1-chloro-2,3-propylene
1,6- and 2,5-hexylene
2,3-diphenyl-1,4-butylene
1-(methoxycarbonyl)-1,5-pentylene
1-carboxy-1,5-pentylene
2,7-heptylene
3-methyl-1,6-hexylene
—$CH_2CH_2OCH_2CH_2$—
—$CH_2CH_2SCH_2CH_2$—
—$CH_2CH_2SSCH_2CH_2$—

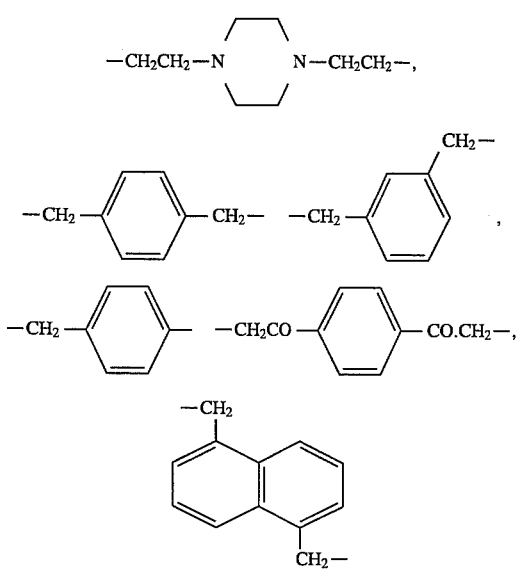

As examples of arylene radicals represented by B there may be mentioned 1,2-, 1,3- and 1,4-phenylene and 1,4-naphthylene which are optionally sulphonated.

The optional substituent which may be present on D is preferably a $C_{1-4}$-alkyl or $C_{1-4}$-alkoxy group.

As examples of particularly useful dyes within the scope of the invention there may be mentioned water-soluble dyes of Formulae (3), (4) or (5) and salts thereof:

$B^1$ and $B^2$ are each independently a divalent organic linking group as hereinbefore defined for B.

In Formulae (3) and (4), Z is preferably a triazinyl group having a labile substituent as discussed above.

The dyes of the invention may be prepared by reactions analogous to those which are known in the preparation of fibre-reactive triphenodioxazine dyes having chloro atoms at both the 6- and 13-positions, except that intermediates are used which result in the 6- and 13-positions having substituents as described herein for the present invention. Thus, for example, dyes of the invention may be prepared by condensation of an acylating agent and an acylatable TPD compound having a chloro or bromo atom at one of the 6- and 13-positions and a group of Formula (1) at the remaining 6- or 13-position. An acylatable TPD compound has an amino, hydroxy or thio substituent, e.g. —$NH_2$, —OH or —SH. Condensation is preferably performed in the presence of base, for example an alkali metal hydroxide, carbonate or bicarbonate, preferably in aqueous solvent, for example water. Preferably the condensation is performed at a temperature in the range 0° to 60° C.; a pH of from 7 to 10 is preferred.

Suitable acylating agents particularly include cyanuric chloride or fluoride and its primary condensation products with ammonia, primary or secondary amines, alcohols or mercaptans.

Compounds of Formula (4) may be prepared by condensing a dyebase of Formula (4), wherein in place of Z there is H, with an acylating agent, preferably of formula Z-Cl, wherein Z is a heterocyclic reactive group, preferably using the above described conditions.

Formula (3):

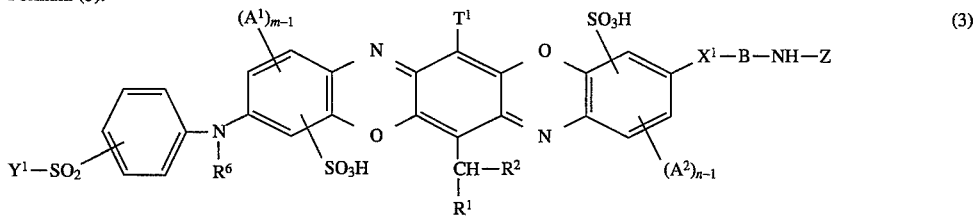

Formula (4):

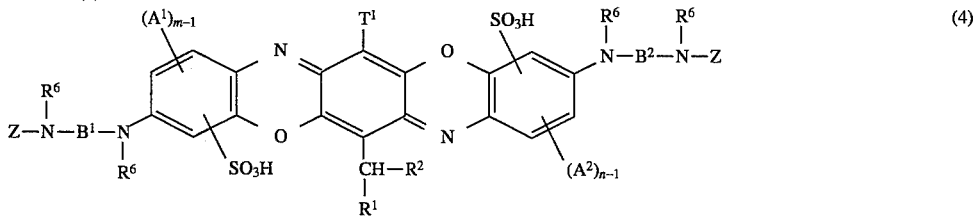

Formula (5):

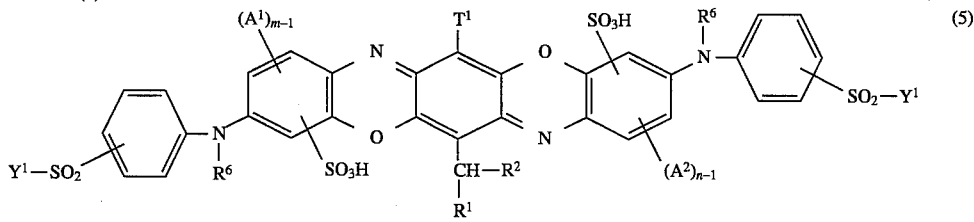

wherein:

$T^1$, $Z$, $A^1$, $A^2$, $X^1$, $B$, $R^1$, $R^2$ and $Y^1$ are as hereinbefore defined;

m and n are each independently 1, 2 or 3;

each $R^6$ independently is H or $C_{1-4}$-alkyl; and

Suitable acylatable TPD compounds containing an amino, hydroxy or thio group may be obtained by methods analogous to those described in the art, for example by ring closure of the corresponding dianilides using strongly acid condensing agents, for example oleum with a persulphate a reaction time of 1 to 24 hours, especially 2 to 10 hours is preferred. Sulphonic acid groups may be introduced into the dianilide during cyclisation, for example into any aryl groups which may be present. Cyclisation conditions may also convert beta-hydroxyethyl sulphonyl groups, when present, to beta-sulphatoethylsulphonyl groups.

Thus the acylatable TPD compounds may be prepared by ring closure of a dianilinide of Formula (6) using oleum and a persulphate:

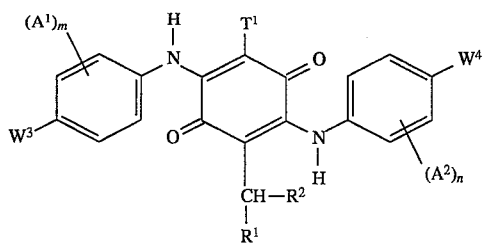

wherein:

$W^3$ and $W^4$ are each independently $-X^1-(B-X^2)_p-H$ or $-X^1-(B-X^2)_q-D-SO_2-Y^2$; and $T^1$, $R^1$, $R^2$, $A^1$, $A^2$, $X^1$, $X^2$, B, D, m, n, p and q are as hereinbefore defined and $Y^2$ is vinyl or 2-hydroxyethyl.

The dianilinides of Formula (6) may be prepared by condensation of monoanilinide of Formula (7) (where B is Cl or Br), with a compound of Formula (8). It is preferred that the condensation is carried out in a solvent, such as water or methanol, at a pH of approximately 6 (e.g. pH 5.5 to 6.5), and at elevated temperatures of around 50° C. (e.g. 40°–60° C.) for a period of several hours (e.g. 0.5 to 24 hours).

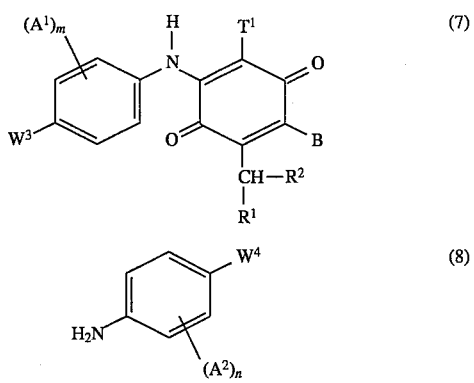

The monoanilinides of Formula (7) may themselves be prepared by an analogous process to that described in European Patent Specification 0356014 A1, particularly page 10 line 25 to page 12 line 20. Typically a para-substituted aniline derivative is condensed with 3,5,6-trihalo-1,4-benzoquinone having a substituent of Formula (1) at the 2-position. It is preferred that the condensation takes place in a solvent, e.g. methanol or water, a temperature of 18° C. to 50° C. is normally employed, and a pH of approximately 5–6 over a period of 0.5 to 24 hours is normally sufficient.

The 3,5,6-trihalo-1,4-benzoquinone having a substituent of Formula (1) at the 2-position may be prepared by bubbling chlorine gas through or adding bromine to a hot aqueous sulphuric acid solution of an aniline compound having a substituent of Formula (1) at the 2- or 3-position. 3,5,6-trihalo-1,4-benzoquinones having a substituent of Formula (1) at the 2-position and their use in the preparation of dyes, especially triphenodioxazine dyes, form a further feature of this invention; preferably the halo is chloro or bromo.

The dyes prepared as described above may be isolated by any conventional means, for example by spray drying or precipitation and filtration.

Dyes according to the invention preferably contain sulphonic acid groups which confer water-solubility and may be isolated with such groups in the free acid form. However, it is usually found more convenient to isolate the dyes in the form of salts particularly alkali metal salts, especially sodium or mixed sodium/lithium salt.

The dyes of the present invention may be used for colouring a wide range of textile materials containing hydroxyl or amino groups, for example wool, silk, leather, synthetic polyamides and natural or regenerated cellulose, for example cotton or viscose rayon materials, by a method comprising applying thereto a dye according to the invention (preferably as a solution in water). Conventional dyeing, padding or printing methods may be used for colouring such materials. In the case of cellulose, the dyes are preferably applied in conjunction with a treatment with an acid binding agent, for example caustic soda, sodium carbonate, phosphate, silicate or bicarbonate, which may be applied to the cellulose textile materials before, during or after the application of the dye.

The dyes of the present invention are particularly valuable dyes for cellulosic materials and have good dyeing properties, for example good wash-off, low cross staining of adjacent fibres during domestic washing or level dyeing. They generally yield bright blue coloured textiles with good resistance to washing and light. They are usually characterised by good solubility in water and salt solutions and an ability to build-up to high depths of shade, the shades being somewhat redder than those of the 6,13-dichlorotriphenodioxazine reactive dyes.

A further feature of the present invention provides a composition comprising an inert carrier and a water-soluble dye according to the invention, preferably in a weight ratio of 1:99 to 99:1, more preferably 50:1 to 1:50, especially 20:1 to 1:20. The inert carrier preferably comprises inorganic salts and optionally a de-dusting agent. Examples of inorganic salts include alkali and alkali earth metal halides, carbonates, bicarbonates, nitrates and mixtures thereof. Dodecylbenzene may be used as a de-dusting agent.

The present invention also provides liquid dye formulations comprising at least five parts, and preferably at least 10 parts of a reactive dye according to the invention dissolved in 100 parts of water. It is preferred that such liquid dye formulations contain total inorganic salts in a percentage of less than 30%, more preferably less than 10%, especially 0.5%, wherein the % figure is expressed as grammes of inorganic salt in volume of 100 cm³. The term "inorganic salts" means any of the salts resulting from the dye manufacturing processes and commonly found in liquid dye formulations, for example NaCl, KCl, $Na_2SO_4$ etc.

Inorganic salts can be substantially removed from the liquid dye formulations using conventional means, for example by a membrane separation process such as reverse osmosis.

The invention is illustrated but not limited by the following Examples in which all parts and percentages are by weight unless otherwise indicated.

EXAMPLE 1

Preparation of

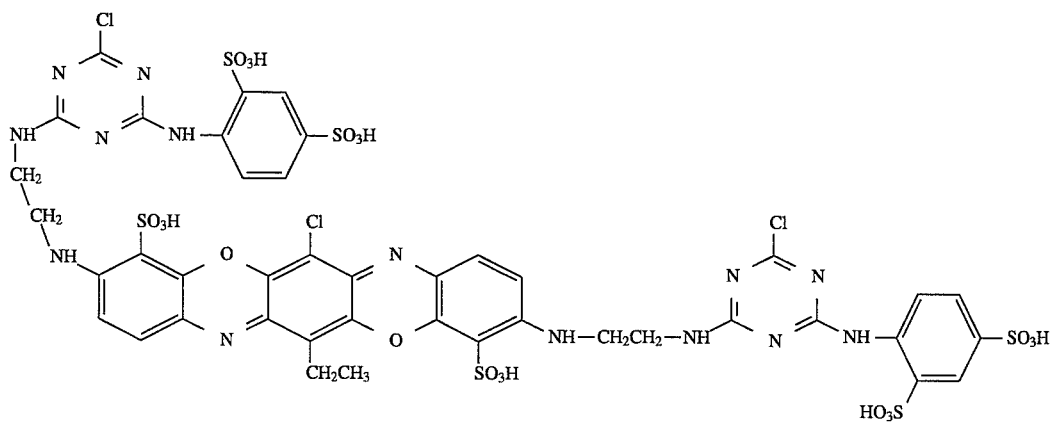

Stage a—Preparation of trichloroethyl-p-benzoquinone 2-ethylaniline (60.5 g) in 60% $H_2SO_4$ (600 ml) was heated to 100° C. Chlorine gas was bubbled into the solution until there was no further uptake and a solid had precipitated. The reaction mixture was drowned onto ice (3 kg) and the precipitated solid collected. Crystallisation from ethanol gave trichloroethyl-p-benzoquinone (35 g) m.p. 115° C.

Stage b—Preparation of Dianilide

Trichloroethyl-p-benzoquinone (15 g) and 2-(2'-aminoethylamino)-5-aminobenzene sulphonic acid (2.1 molecular equivalents) were stirred together in water (500 ml) at 50° C. and pH 6. A few drops of calsolene oil were added. The pH was maintained between 5–6 by addition of $Na_2CO_3$ solution. After 5 hours at 50° C. the mixture was cooled and a brown/black precipitate of dianilide collected (37 g).

Stage c—Ring Closure of Dianilinide to give an acylatable dyebase

Dianilide (37 g) was dissolved in 5% oleum (400 mls) and ammonium persulphate (2 molecular equivalents) added. After 3 hours at room temperature the oleum solution was drowned onto ice (1.5 kg). Acetone (1.5l) was then added and the reddish-blue solid dyebase collected by filtration (12 g), lambda $_{max}$ ($H_2O$) 606 nm.

Stage d—Acylation of dyebase to give Title Product

The dyebase (10 g) was dissolved in water at pH 9. A solution of 2',4'-disulphoanilinodichloro-1,3,5-triazine (3 molecular equivalents) was added and the reaction mixture heated to 50° C. The pH was maintained at pH 8.5 for 3 hours. Salt (to approximately 25% w/v) was added and the precipitated Title Product collected by filtration (25 g, 50% strength), lambda $_{max}$ ($H_2O$) 612 nm. The Title Product was found to have good solubility in water.

The title product was applied to cotton by exhaust dyeing to give a bright reddish-blue colour. The dyed cotton was found to have good fastness properties to washing and light.

EXAMPLES 2 TO 23

Further dyes according to the invention may be prepared by a similar procedure to Example 1 except that in place of 2',4'-disulpho anilinodichloro-1,3,5-triazine there is used the acylating agent listed below:

| Example | Acylating Agent |
| --- | --- |
| 2 | Cyanuric chloride |
| 3 | 2',5'-disulphoanilinodichloro-1,3,5-triazine |
| 4 | 2,4-dichloro-6-beta-hydroxyethylamino-s-triazine |
| 5 | 2,4-dichloro-6-di-beta-hydroxyethylamino-s-triazine |
| 6 | 2,4-dichloro-6-beta-hydroxypropylamino-s-triazine |
| 7 | 2,4-dichloro-6-methoxy-s-triazine |
| 8 | 2,4-dichloro-6-amino-s-triazine |
| 9 | 2,4-dichloro-6-methylamino-s-triazine |
| 10 | 2,3-dichloroquinoxaline-6-sulphonyl chloride |
| 11 | 2,4,5,6-tetrachloropyrimidine |
| 12 | 2,4,6-trichloropyrimidine |
| 13 | 1,4-dichlorophthalazine-6-carbonyl chloride |
| 14 | 2,4,6-trichloro-5-cyanopyrimidine |
| 15 | 2,4,6-trifluoro-5-chloropyrimidine |
| 16 | 1-(4'-chlorocarbonylphenyl)-4,5-dichloro-6-pyridazone |
| 17 | 2,4,6-tribromopyrimidine |
| 18 | 2,4-dichloro-6-beta-sulphatoethylamino-s-triazine |
| 19 | 2-(2',4'-dichloro-s-triazinylamino)-5-(2'-chloro-4'-meta-sulphoanilino-s-triazinylamino)benzene sulphonic acid |
| 20 | 2-(2',4'-dichloro-s-triazinylamino)-5-(2'-chloro-4'-amino-s-triazinylamino)benzene sulphonic acid |
| 21 | 2'-carboxy-4'-sulphoanilinodichloro-1,3,5-triazine |
| 22 | 3'-β-sulphatoethylsulphoanilinodichloro-1,3,5-triazine |
| 23 | 5-chloro-4,6-difluoropyrimidine |

EXAMPLES 24 TO 41

Further dyes according to the invention may be prepared by the method of Example 1 except that in place of 2',4'-disulphoanilinodichloro-1,3,5-triazine there is used an equivalent amount of an acylating agent formed by the reaction of cyanuric chloride with one equivalent of each of the amines listed in the table below:

| Example | Amine |
| --- | --- |
| 24 | $H_2NCH_2CH_2Cl$ |
| 25 | $H_2NCH_2CH_2CH_2OCH_3$ |
| 26 | 2,4-dichloroaniline |
| 27 | 2-amino-4-sulphotoluene |
| 28 | 1-amino-6-chloro-3-sulphobenzene |
| 29 | 1-amino-2,4-dimethoxy-6-sulphobenzene |
| 30 | N-methyl-p-toluidine |
| 31 | N-ethyl-2-ethylaniline |
| 32 | N-ethyl-2,5-dimethylaniline |
| 33 | 2-sulpho-4-methylaniline |
| 34 | 2-sulpho-5-methylaniline |
| 35 | 3-sulpho-5-chloroaniline |
| 36 | 3-sulpho-6-ethoxyaniline |
| 37 | N-sulphomethylaniline |
| 38 | N-β-hydroxyethylaniline |
| 39 | N-β-cyanoethylaniline |
| 40 | $H_2N(CH_2CH_2O)_2CH_2CH_2OH$ |

| Example | Amine |
|---|---|
| 41 | Mixture of 3- and 4-sulphoaniline |

EXAMPLE 42

Preparation of

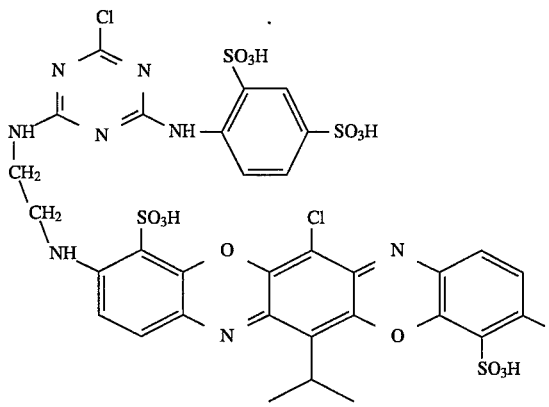

Stage a)

2-isopropylaniline (100 g) in 70% $H_2SO_4$ (1200 ml) was heated to 70° C. Chlorine gas was bubbled into the solution until there was no further uptake and a solid had precipitated. The reaction mixture was drowned onto ice (2 kg) to precipitate isopropyltrichloro-p-benzoquinone as a reddish-brown solid (94 g). (Analysis: C42.4%; H3.2%; Cl 41.1%. $C_9H_7Cl_3O_2$ requires C42.6%; $H_{2.8}$%; Cl42.0%).

Stage b)

Isopropyltrichloro-p-benzoquinone (20 g) and 2-(2'-aminoethyl amino)-5-aminobenzene sulphonic acid (2.1 molar equivalents) were stirred together in water (500 ml) at 80° C. and pH6. A few drops of calsolene oil were added. The pH was maintained between 5–6 by addition of $Na_2CO_3$ solution. After 12 hours at 80° C. the mixture was cooled and a brown precipitate of dianilide collected (25 g).

Stage c)

The product from stage b) (15 g) was dissolved in 10% oleum (165 ml) and potassium sulphate (2 molar equivalents) added. After 4 hours at room temperature the oleum solution was drowned into ice (2.5 kg) to give a reddish-blue solid dyebase which was collected by filtration (4 g).

Stage d)

The product from stage c) (4 g) was dissolved in water at pH9. A solution of 2',4'-disulphoanilinodichloro-1,3,5-triazine (3 molar equivalents) was added and the mixture heated

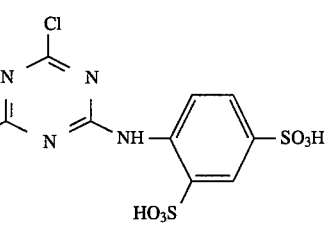

to 50° C. The pH was maintained at 8.5 for 3½ hours. Salt (to approximately 25% w/v) was added and the precipitated title product collected by filtration (9 g, 41% strength), lambda $_{max}(H_2O)$ 605 nm.

The title product was applied to cotton by exhaust dyeing and the resultant dyed fabric was found to have good fastness to washing and light.

EXAMPLES 43 TO 82

Further dyes may be prepared by following the method of Examples 2 to 41 except that in place of the dyebase from Example 1, stage c), there is used an equivalent amount of the dyebase from Example 42, stage c).

EXAMPLE 83

Preparation of

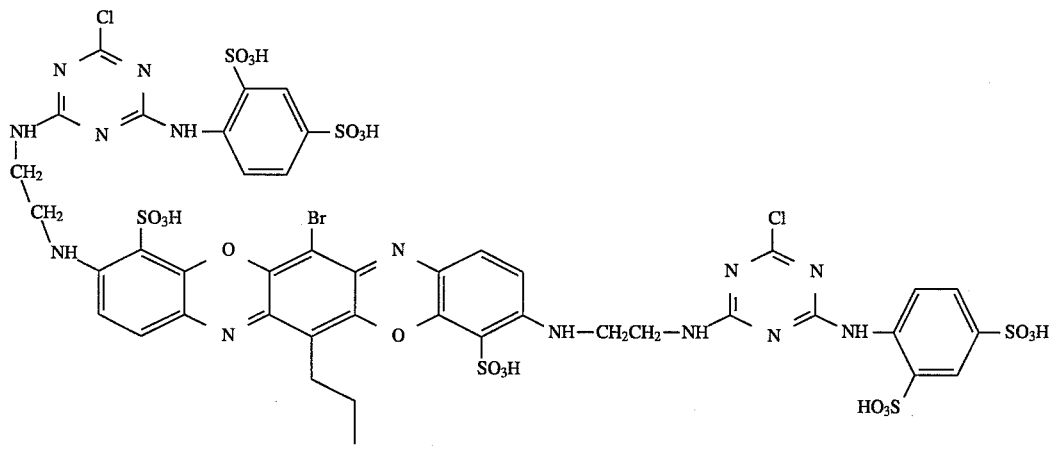

Stage a)

Manganese dioxide (45 g) was stirred in 25% H₂SO₄ (1300 ml) at room temperature. 2-propylphenol (90 g) was added followed by manganese dioxide (270 g), added over 1 hr to maintain a reaction temperature below 50° C. After a further 1½ hours the reaction mixture was steam distilled, the distillates extracted with chloroform and the chloroform evaporated to yield propyl-p-benzoquinone (7 g), delta H(CDCl₃) 1.00 (3H, t, J8.0H$_z$), CH₃), 1.57(2H, tq, J 8.0, 8.0H$_z$, CH₂), 2.42(2H,t,J 8.0H$_z$, CH₂), 6.58–6.82 (3H, m, CH).

Stage b)

Propyl-p-benzoquinone (7 g) was stirred in glacial acetic acid (70 ml) and bromine (17.5 ml) added. After 3 hours at 70° C. the reaction mixture was drowned into water (500 ml) and extracted with ethylacetate. The organic extracts were back-washed with 5% sodium metabisulphite and evaporated to yield propyltribromo-p-benzoquinone (17 g), delta H(d⁶-DMSO) 0.97 (3H, t, J 8.0H$_z$, CH₃), 1.48 (2H, tq, J 8.0, 8.0H$_z$), 2.62 (2H, t, J 8.0H$_z$, CH₂).

Stage c) Preparation of Dianilide

Propyltribromo-p-benzoquinone (15 g) and 2-(2'-aminoethyl amino)-5-aminobenzene sulphonic acid (2.1 molar equivalents) were stirred together in water (500 ml) at 75° C. and pH6. The pH was maintained between 5–6 by addition of Na₂CO₃ solution. After 10 hours at 75° C. the mixture was cooled and a brown solid collected (8 g).

Stage d) Ring Closure of Dianilide

The product from stage c) (8 g) was dissolved in 10% oleum (80 ml) and potassium persulphate (2 molar equivalents) added. After 4 hours at room temperature the oleum solution was drowned onto ice (1.5 kg) and the reddish-blue dyebase collected by filtration (2 g).

Stage e) Acylation of dyebase

The dyebase from stage d) (2 g) was dissolved in water (150 ml) at pH9. A solution of 2',4'-disulphoanilinodichloro-1,3,5-triazine (3 molar equivalents) was added and the reaction mixture heated to 50° C. The pH was maintained at pH 8.5 for 4 hours. Salt (to approximately 30% w/v) was added and the precipitated title product collected by filtration (1.5 g, 37% strength), lambda$_{max}$ (H₂O) 596 mm.

The title product was applied to cotton by exhaust dyeing and the resultant dyed fabric was found to have good fastness to washing.

EXAMPLES 84 TO 123

Further dyes may be prepared by following the method of Examples 2 to 41 except that in place of the dyebase from Example 1, stage c), there is used an equivalent amount of the dyebase from Example 83, Stage d).

EXAMPLE 124

Preparation of

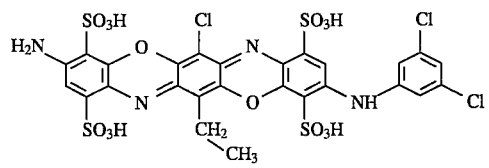

Stage a)

Ethyltrichloro-p-benzoquinone (4.8 g) and p-phenylenediamine disulphonic acid (2 mole equivalents) were stirred together in water (300 ml) at 50° C. and pH6.5. The pH was maintained at 6–7 by addition of Na₂CO₃ solution. After 4 hours the temperature was increased to 80° C. for 8 hours. The solution was evaporated to give a brown solid (19 g, 68% strength).

Stage b)

The product from Stage a) (13 g, 68% strength) was dissolved in 20% oleum (63 ml) at room temperature and potassium persulphate (2 mole equivalents) added. After two hours at 20°–25° C. the reaction temperature was raised to 45°–50° C. for 8 hours. The reaction mixture was drowned into ice (300 g), salt added, and the reddish-blue solid dyebase collected by filtration (4 g, 42% strength).

Stage c)

The dyebase from Stage b) (4 g, 42% strength) was dissolved in water (375 ml) at pH8.5 and the solution cooled to 0°–10° C. Cyanuric chloride (1.1 mole equivalents) was added. The pH was maintained at pH8 for 5 hours. Salt was added (to approximately 30% w/v) and the title product collected by filtration (3.5 g, 18% strength).

EXAMPLES 125 TO 165

Further dyes may be prepared according to the method of Example 124 except that in place of cyanuric chloride there is used an equivalent amount of each of the acylating agents used in Examples 1 and 3 to 41 above.

EXAMPLE 166

Preparation of

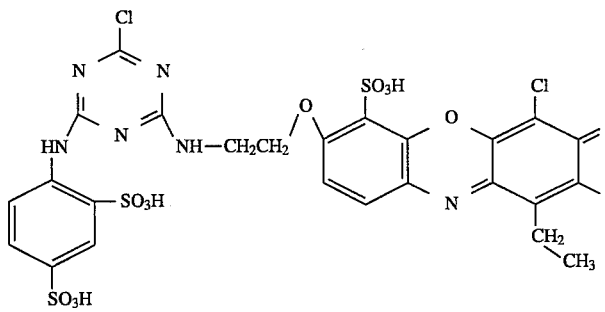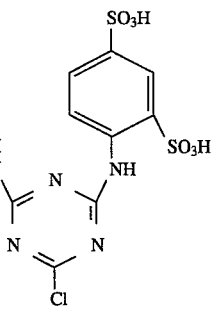

Stage a)

Ethyltrichloro-p-benzoquinone (5.6 g) and 2-(2'-aminoethoxy)-5-aminobenzene sulphonic acid (2.1 mole equivalents) were stirred together in water (100 ml) at 80° C. and pH6.5. A few drops of calsolene oil were added. The pH was maintained at 6–7 by addition of Na₂CO₃ solution. After 4 hours at 80° C. the mixture was cooled and a brown precipitate of dianilide collected (7.8 g).

Stage b)

The product from Stage a) (7.8 g) was dissolved in 20% oleum (50 ml) and potassium persulphate (2 mole equivalents) were added. After 1½ hours at 30° C. the oleum solution was drowned onto ice (500 g) and a purple solid dyebase collected by filtration (4.3 g).

Stage c)

The dyebase from Stage b) was dissolved in water (200 ml) at pH9. A solution of 2',4'-disulphoanilinodichloro-1,3,5-triazine (3 mole equivalents) was added and the reaction mixture heated to 50° C. The pH was maintained at pH 8.5 for 3 hours. KCl (to approximately 30% w/v) was added and the precipitated title product collected by filtration (7.8 g, 37% strength), lambda$_{max}$ (H$_2$O) 506, 540 nm.

EXAMPLES 167 TO 206

Further dyes may be prepared by following the method of Example 166 except that in place of 2',4'-disulphoanilinodichloro-1,3,5-triazine used in Stage c) there is used an equivalent amount of each of the acylating agents used in Examples 2 to 41 above.

EXAMPLE 207

Preparation of

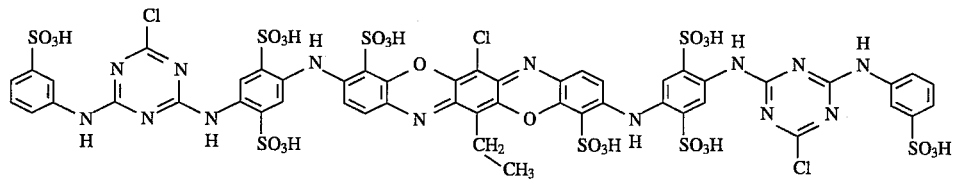

Stage a)

Ethyltrichloro-p-benzoquinone (3.6 g) and 4,4'-diaminodiphenyl amine-2,2',5-trisulphonic acid (2.1 mole equivalents) were stirred together in water (110 ml) at 50° C. and pH6. A few drops of calsolene oil were added. The pH was maintained between 5.5 and 6 by addition of a Na$_2$CO$_3$ solution. After 4 hours at 50° C. the mixture was cooled, screened and saturated with salt. A dark brown precipitate of dianilide was collected (18.8 g)

Stage b)—dichlorotriazinyl dye

The product from Stage a) (18.6 g) was dissolved in 98% H$_2$SO$_4$ and manganese dioxide (7 g) added. After 1 hour at room temperature the solution was drowned onto ice (1.2 kg). KCl solution (to approximately 25% w/v) was added and the pH adjusted to pH 11. The precipitated dyebase was collected by filtration and redissolved in cold water (1000 ml). The solution was adjusted to pH7 and cyanuric chloride (2.8 g) added. A few drops of calsolene oil were added. The pH was maintained between 6.5-7 by addition of Na$_2$CO$_3$ solution. After 4 hours at 5° C. the blue solution was reduced in volume, dialysed and evaporated to a blue powder (42.8 g, 11% strength).

Stage c)

The product from Stage b) (21 g) and metanilic acid (3.5 g) were dissolved in water (150 ml). pH7 was maintained by addition of Na$_2$CO$_3$ solution. After 4 hours at room temperature the solution was dialysed and water evaporated to yield to the title product (6.3 g, 50% strength) lambda$_{max}$ (H$_2$O) 588 nm.

EXAMPLES 208 TO 225

The method of Example 207 may be repeated except that in place of metanilic acid there is used an equivalent amount of each of the amines used in Examples 24 to 41.

EXAMPLE 226

Preparation of

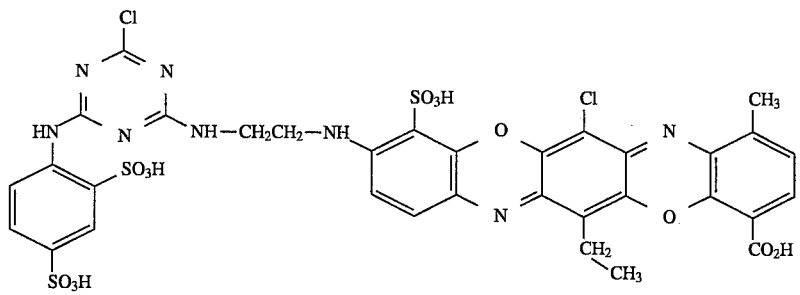

Stage a)

Ethyltrichloro-p-benzoquinone (13 g) was stirred in methanol (800 ml) and water (20 ml) at 40° C. and pH 5-6. 3-Amino-4-methylbenzoic acid (7.5 g) was added portionwise over 1 hour while maintaining the pH between 5.5 and 6 by addition of Na$_2$CO$_3$ solution. After 36 hours at 40° C. the reaction mixture was evaporated to give a red-brown solid monoanilide (22.9 g).

Stage b)

The monoanilide from stage a) (9.2 g) was stirred in tetrahydrofuran:methanol:water (1:1:1) (300 ml) at 0°–10° C. and pH 6.5-7. 2-(2'-aminoethylamino)-5-aminobenzene sulphonic acid (1.1 mole equivalents) was added and the reaction mixture stirred at 10° C. and pH 6.5 until the reaction was complete. The brown/black precipitate of dianilide was collected by filtration (12.5 g, 55% strength).

Stage c)

Dianilide from stage b) was dissolved in 10% oleum (110 ml) at 10°–20° C. Potassium persulphate (2 mole equivalents) was added and the reaction mixture warmed to 55° C. for 4 hours then drowned onto ice. The resultant reddish-blue dyebase was collected by filtration (2.6 g, 82% strength).

Stage d)

The dyebase from Stage c) (2 g) was dissolved in water (90 ml) at pH9. A solution of 2',4'-disulphoanilinodichloro-1,3,5-triazine (1.5 mole equivalents) was added and the reaction mixture heated to 50° C. The pH was maintained at 8.5–9 for 3 hours. Salt (to approximately 30% (w/v)) was added and the precipitated title product collected by filtration (5.7 g, 7% strength) lambda$_{max}$ (H$_2$O) 568 nm.

EXAMPLES 227–266

The method of Example 226 may be repeated except that in place of 2',4'-disulphoanilinodichloro-1,3,5-triazine used in Stage d) there is used an equivalent amount of each of the acylating agents described in Examples 2 to 41 respectively.

EXAMPLE 267

Preparation of:

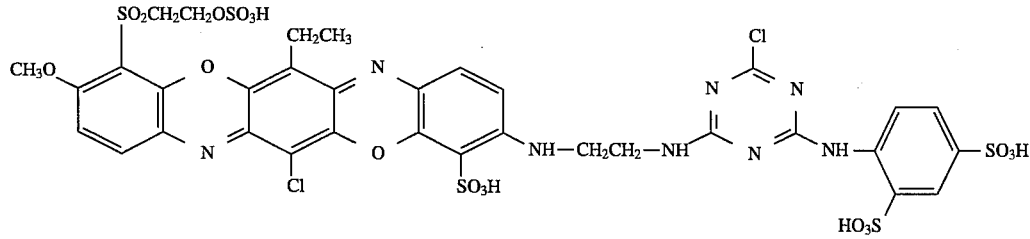

The method of Example 226 was repeated except that in place of 3-amino-4-methylbenzoic acid there was used 1 equivalent of 3-(β-hydroxyethylsulphone)-4-methoxyaniline to give the title compound having a lambda max in water at 552 nm.

EXAMPLE 268

Preparation of:

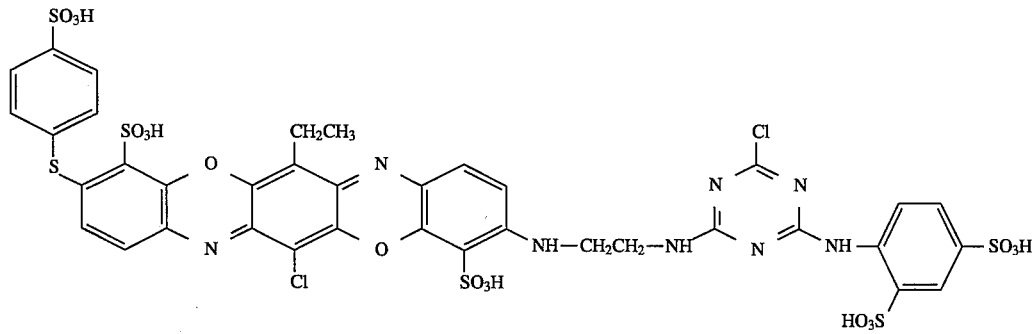

The method of Example 226 was repeated except that in place of 3-amino-4-methylbenzoic acid acid there was used 1 equivalent of 3-amino-4-phenylmercaptobenzenesulphonic acid to give the title compound having a lambda max in water at 596 nm.

EXAMPLE 269

Preparation of:

[Structure diagram shown at top of page]

The method of Example 226 was repeated except that in place of 3-amino-4-methylbenzoic acid there was used 1 equivalent of 3-amino-4,6-dimethoxybenzene diethylsulphonamide to give the title compound having a lambda max in water at 555 nm.

EXAMPLE 270

Preparation of:

[Structure diagram]

The method of Example 1, stages a to c, may be repeated except that in place of 2-(2'-aminoethylamino)-5-aminobenzene sulphonic acid there is used 3-(β-hydroxyethylsulphone)-4-(β-hydroxyethylamino)aniline.

I claim:

1. A water-soluble dye of the Formula (2) or salt thereof:

[Formula (2) structure]

wherein:

$T^1$ is Cl or Br;

each $A^1$ and $A^2$ independently is alkyl, alkoxy, Cl, Br, carboxy, or —$SO_2$—Y;

each Y independently is —$OR^3$, —$NR^3R^4$, vinyl a group convertible to vinyl on treatment with aqueous alkali, or alkyl;

each $R^3$ and $R^4$ independently is hydrogen or aryl;

m and n are each independently 0, 1, 2 or 3;

$W^1$ and $W^2$ are each independently a fibre-reactive group of the formula —$X^1$—($B^2$—$X^2$)$_p$—Z;

$X^1$ and $X^2$ are —$NR^5$— wherein $R^5$ is H or $C_{1-4}$-alkyl;

$B^2$ is a divalent organic linking group;

p is 0 or 1;

Z is a heterocyclic reactive group;

$R^1$ is H, OH or $CH_3$; and $R^2$ is $C_{1-3}$-alkyl, hydroxy-$C_{1-3}$-alkyl or —$CH_2O$—($C_{1-4}$-alkyl).

2. A dye according to or claim 1 wherein the group $$\begin{array}{c} | \\ CH-R^2 \\ | \\ R^1 \end{array}$$

is selected from —$CH_2CH_3$, —$CH_2CH_2CH_3$, —$(CH_2)_3$—$CH_3$, —$CH_2CH(CH_3)_2$, —$CH(CH_3)_2$, —$CH_2CH_2$—O—$CH_3$, —$CH_2CH_2$—$OCH_2CH_3$, —$CH(OH)CH_3$ and —$CH_2CH_2OH$.

3. A water-soluble dye according to claim 1 of the Formula (4) and salts thereof:

[Formula (4) structure]

wherein:

$R^1$, $R^2$, $T^1$, $A^1$ and $A^2$ are as defined in claim 1;

m and n are 1, 2 or 3;

$B^1$ and $B^2$ are each independently an alkylene;

each $R^6$ independently is H or $C_{1-4}$-alkyl; and each Z independently is a heterocyclic reactive group.

4. A water-soluble dye according to claim 3 wherein $B^1$ and $B^2$ are each independently $C_{1-6}$-alkylene.

5. A water-soluble dye according to claim 3 wherein $R^1$ is H or $CH_3$; $R^2$ is $C_{1-3}$-alkyl; $T^1$ is Cl or Br; m and n are 1; $B^1$ and $B^2$ are each independently $C_{2-4}$-alkylene-; each $R^6$ is H or $C_{1-4}$-alkyl and each Z independently is a triazin-2-yl group having a labile substituent at one or both of the 4- and 6-positions.

6. A water-soluble dye according to claim 5 wherein $B^1$ and $B^2$ are each independently $C_{2-4}$-alkylene and each Z independently is a triazin-2-yl group having a labile substituent selected from F, Cl, 3-carboxypyridinium and 4-carboxypyridinium at one or both of the 4- and 6-positions.

7. A process for colouring a textile comprising applying thereto a dye according to claim 1.

8. A liquid dye formulation which contains less than 30% inorganic salts, comprising at least five parts of a reactive dye according to claim 1 dissolved in 100 parts of water.

9. A water-soluble dye according to claim 1 of the following formula and salts thereof:

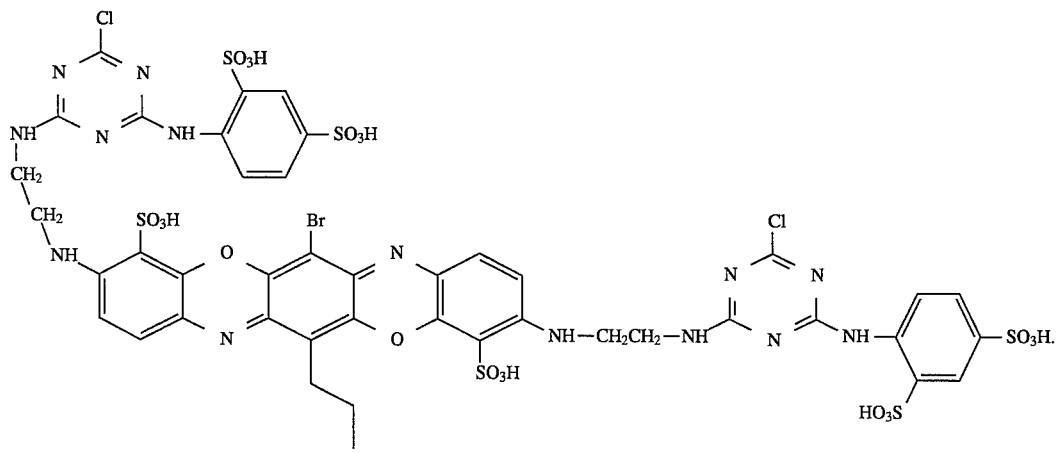

10. A water-soluble dye of the following formula and salts thereof:

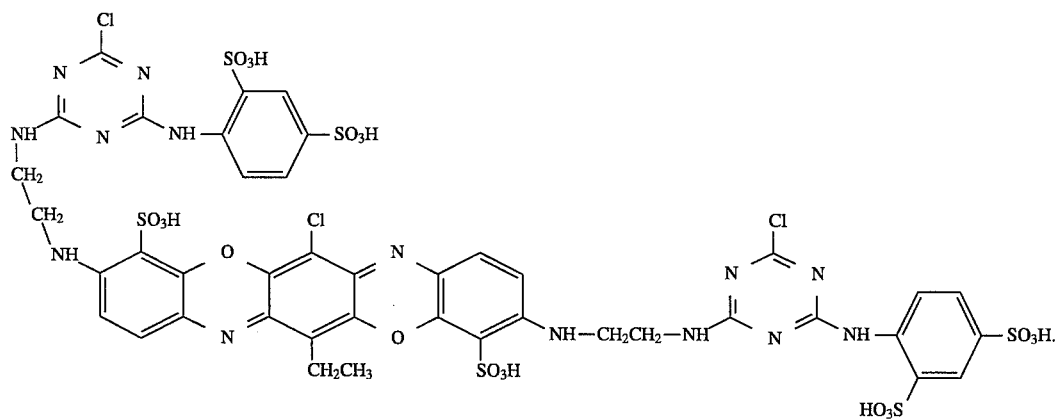

11. A water-soluble dye according to claim 1 of the following formula and salts thereof:

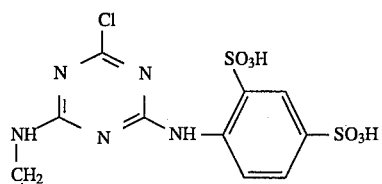
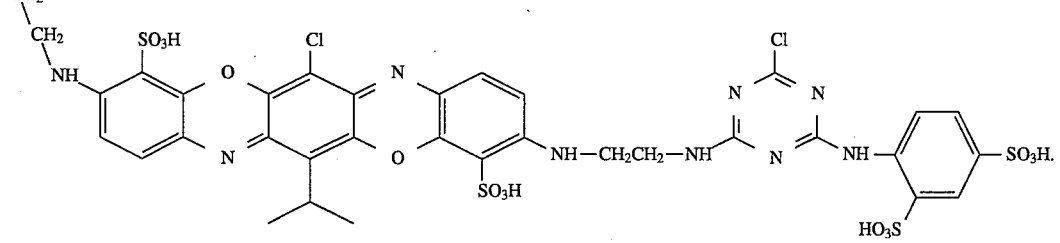
* * * * *